United States Patent
Schelong et al.

(12) 
(10) Patent No.: US 6,322,993 B1
(45) Date of Patent: Nov. 27, 2001

(54) METHOD FOR THE DETERMINATION OF LIPASE

(75) Inventors: Lieselotte Schelong, Tutzing; Ralf Zielenski, Bichl; Urban Prinzing, Peissenberg, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/068,611
(22) PCT Filed: Sep. 16, 1997
(86) PCT No.: PCT/EP97/05051
§ 371 Date: May 8, 1998
§ 102(e) Date: May 8, 1998
(87) PCT Pub. No.: WO98/12350
PCT Pub. Date: Mar. 26, 1998

(30) Foreign Application Priority Data

Sep. 19, 1996 (DE) ............................................. 196 38 271
Aug. 1, 1997 (DE) ............................................. 197 33 309

(51) Int. Cl.$^7$ .............................. C12Q 1/00; C12Q 1/44; C12Q 1/34; G01N 33/53
(52) U.S. Cl. ................................. 435/19; 435/18; 435/4; 435/968; 435/7.72; 435/7.71
(58) Field of Search ................... 435/19, 18, 4, 435/968, 7.72, 7.71

(56) References Cited

U.S. PATENT DOCUMENTS 3,786,140 * 1/1974 Meyer-Bertenrath et al. ......... 435/18

FOREIGN PATENT DOCUMENTS

0101046 * 2/1984 (EP).
0207252 * 4/1987 (EP).
9812350 * 3/1998 (WO).

OTHER PUBLICATIONS

Okahata et al; Bull. Chem. Soc. Jpn, vol. 65, pp. 2411–2420, (1992).*

* cited by examiner

Primary Examiner—Louise N. Leary
(74) Attorney, Agent, or Firm—Marilyn L. Amick; Roche Diagnostics Corporation

(57) ABSTRACT

The invention concerns a method and reagent for the determination of lipase in the presence of a colour substrate and at least one N-substituted carboxylic acid amide derivative or a compound of the general formula (I) or (Ia)

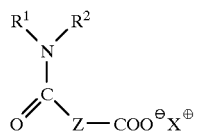

(I)

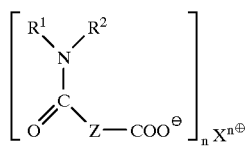

(Ia)

in which $R^1$ and $R^2$ independently of one another represent hydrogen or a saturated or unsaturated, substituted or unsubstituted hydrocarbon residue with 2 to 24 carbon atoms, Z denotes a saturated or unsaturated, substituted, cyclic or straight-chained hydrocarbon residue with 1 to 10 carbon atoms, X represents an atom or a group of atoms with positive charge and n is a number from 1 to 3. Tetra-sodium-N-(1,2-dicarboxylethyl)-N-alkylsulfosuccinamide or a mixture containing such a compound has proven to be particularly advantageous for the elimination of unspecific reactions in the determination of lipase in a biological sample.

20 Claims, 4 Drawing Sheets

METHOD FOR THE DETERMINATION OF LIPASE

This is a Section 371 PCT/EP97/05051 filed Sept. 16, 1997.

The invention concerns a method and reagent for the determination of lipase in biological liquids as well as the use of a lower molecular N-substituted carboxylic acid amide derivative to eliminate unspecific reactions in the determination of enzymes. In particular it has proven to be advantageous when N-(1,2-dicarboxylethyl)-N-alkyl-sulfosuccinamide or N-(1,2-dicarboxylethyl)-N-alkylaryl-sulfosuccinamide derivatives are present at a concentration of ca. 0.001 to 2.0% (w/v).

The determination of lipase and in particular of human pancreatic lipase (E.C. 3.1.1.3.) has for a long time been of undisputed importance for the diagnosis and assessment of the course of pancreatic diseases (W. Steinberg et al., Annals of Internal Medicine 102 (1985), 576; M. Panteghini et al., Clin. Biochem. 24 (1991), 497; N. W. Tietz and D. F. Shuev. Clin. Chem. 39/5 (1993), 746). For example in acute pancreatitis an increase of the lipase in serum occurs within a few hours which is sometimes very massive.

The function of lipase in the body is essentially to cleave preferably α ester bonds of triglycerides containing long chained fatty acid esters into a diglyceride component and the free fatty acid. Subsequently conversion to the monoglyceride takes place but considerably more slowly.

Usually enzyme-catalysed reactions proceed in an aqueous phase: however, due to its physiological importance, lipase only reacts at the oil/water interlace. In this respect it differs significantly from the esterases. Furthermore lipases can only attach to an interface emulsified by bile acids without denaturation and to cleave triglycerides with the aid of colipase. For this reason the reaction kinetics are substantially influenced by the quality of the interface presented to the enzyme in addition to chemical parameters.

Nowadays various methods are known for the determination of lipase. These are essentially titrimetric, turbidimetric and immunological test principles. In the titrimetric determination an excess of lipase substrate, such as for example olive oil, is added first and the amount of fatty acid released from this by the lipase is measured by titration with alkali using an indicator or by extracting the corresponding copper salts. Titrimetric methods are nowadays only seldom used in routine clinical chemistry laboratories because of the difficult handling in some cases, the long reaction period and the large quantity of sample required (W. Junge in Methods of Enzymatic Analysis, Weinheim VCH, U. Bergmeyer ed., vol. 4 (1984), 15).

The turbidimetric lipase determination in which the clearing of the turbidity of a triglyceride/water emulsion is monitored photometrically is nowadays a widespread method in routine clinical chemical laboratories (W. Rick and M. Hockeborn, J. Clin. Chem. Biochem. 20 (1982), 735; J. Ziegenhorn et al., "Medica Sonderheft" 11 (1980)). A problem with the turbidity measurement is that individual serum samples do not exhibit a linear decrease of the measured signal within the measurement window of the photometer or even exhibit an increase in turbidity. A further difficulty with this method of determination is the reproducible production of an emulsion which always reliably has the same droplet size.

A particular disadvantage of immunological methods is that in this procedure the mass and not the enzyme activity is measured (W. Uhl et al., Internat. J. Pancreatology 12/3 (1992), 253; G. E. Hoffmann et al., Ärztl. Lab. 30 (1984), 193; H. Herden and K. Walter, Klin. Lab. 38 (1992), 89).

Consequently test methods based on a colour development have been developed and are mainly used nowadays. For example 1,2-diglycerides are used as a substrate which are degraded by lipase to 2-mono-glycerides and subsequently cleaved to glycerol by a 2-monoglyceride lipase that is added to the test. The free glycerol that is formed in this manner is degraded with the aid of a glycerol phosphate oxidase to form dihydroxyacetone and hydrogen peroxide ($H_2O_2$). The $H_2O_2$ that is formed is detected by an appropriate colour indicator system (P. Fossati et al., Clin. Chem. 38/2 (1992), 211).

Today it is also possible to directly convert a colour substrate for the determination of lipase (EP 0 207 252). In this method the activity of human pancreatic lipase directly releases a photometrically determinable dye from the substrate which hence avoids a complicated enzyme cascade to produce the dye.

Furthermore it has been known for a long time that the ester bond of the colour substrates used can generate an excessively high signal due to unspecific hydrolysis. For example it is problematic that the colour substrate para-nitrophenyl acetate is hydrolysed by albumin and gamma globulins (W. Downey and P. Andrews, Biochem. J. 96 (1965) 21). Such reactions result in a falsification of the measured value which can lead to a clinically false diagnosis especially in the case of serum samples.

SUMMARY AND OBJECTS OF THE INVENTIONS

The object of the invention is therefore to eliminate unspecific reactions in the determination of lipase and hence to increase the validity of the analytical result.

The object is achieved by a method for the determination of lipase by adding a lipase colour substrate and a lower molecular N-substituted carboxylic acid amide derivative and subsequently photometrically determining the dye released from the substrate. Compounds of the general formula (I) or (Ia) have in particular proven to be suitable according to the invention as the carboxylic acid amide derivative

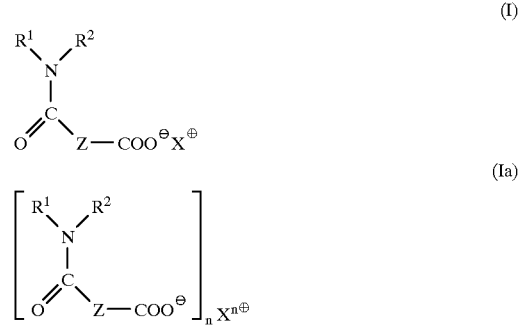

in which $R^1$ and $R^2$ independently of one another represent hydrogen or a saturated or unsaturated, substituted or unsubstituted, optionally carboxylated hydrocarbon residue with 2 to 24 carbon atoms.

Z denotes a saturated or unsaturated, substituted or unsubstituted, cyclic or straight-chained hydrocarbon residue with 1 to 10 carbon atoms, X represents an atom or a group of atoms with positive charge and n is a number from 1 to 3.

Those carboxylic acid amide compounds according to formula (I) or (Ia) are preferred according to the invention, wherein Z is a methylene and/or ethylene group composed of one to ten C atoms and which is optionally substituted by an electron-attracting group such as a carboxyl, sulfonyl, phosphate, phosphonate, nitro, nitrite or nitrate, halogen or alkoxy group, $R^1$ and $R^2$ independently of one another represent hydrogen, an optionally substituted straight-chained or branched, saturated or unsaturated alkyl, aryl, alkylaryl or alkylene group composed of three to 24 C atoms, in which a carboxyl alkyl or dicarboxyl-alkyl residue composed of two to 24 C atoms is particularly preferred and X represents an atom or a group of atoms with a positive charge and n denotes the number 1 or 2, have proven to be suitable.

According to the invention compounds which come into particular consideration are those in which the residue Z carries a carboxyl and/or sulfonyl group but also those in which one of the residues $R^1$ or $R^2$ denotes a lower alkyl group such as for example a methyl, ethyl, propyl, butyl, pentyl, an ethylenyl or propylenyl group or a C 10 to C 18 alkyl group. The substitution of appropriate alkyl or alkylene groups is optionally carried out according to known methods. Furthermore it has proven to be advantageous if $R^1$ for example represents a dicarboxylic acid residue based on malonic acid, glutaric acid, adipic acid, pimelic acid, azelaic acid and sebacic acid and in particular succinic acid. The compounds that can be used according to the invention preferably have a molecular weight of ca. 200 to 1000 Daltons; however, compounds have also proven to be suitable of up to 3000 Daltons. Compounds or salts that have at least two acidic groups have proven to be quite particularly advantageous such as for example the tetrasodium salt based on N-(1,2-dicarboxy-ethyl)-N-alkyl-sulfosuccinamide with a lower alkyl group (1 to 6 C atoms) and/or with a higher alkyl group (12 to 18 C atoms) or N-(1,2-dicarboxyethyl)-N-alkylaryl-sulfosuccinamide or derivatives derived thereof and corresponding mixtures.

In principle all compounds which are recognized and converted by lipase as a substrate can be used for the determination of lipase in the presence of a compound according to the invention such as for example according to the general formula (I) or (Ia). A method for the determination of lipase has proven to be particularly advantageous in which compounds according to ¯EP 0 207 252 are used as the lipase substrate such as for example 1,2-O-dioctyl-rac-glycero-3-azelaic acid, 1,2-O-didecyl-rac-glycero-3-pimelic acid or 1,2-O-didodecyl-rac-glycero-3 -glutaric acid resorufin ester or 1,2-O-dilauryl-rac-glycero-3-glutaric acid-(4'- or 6'-methyl resorufin) ester. In this connection it has surprisingly turned out that the substances according to the invention are able to protect against unspecific hydrolysis in an emulsion which contains a corresponding colour substrate without at the same time inhibiting the activity of lipase.

A compound according to the general formula (I) or (Ia) with the meanings stated above for $R^1$, $R^2$, Z, X and n or a mixture of several compounds according to the invention is added to the reaction solution for the lipase determination at a concentration (final concentration) of approximately 0.001 to 2.0% (w/v) advantageously of ca. 0.01 to 1.0% (w/v).

Further conditions and additives such as for example detergents (e.g. taurodeoxycholate, sodium deoxycholate, polydocanol), substances with bactericidal or fungicidal effect (sodium azide, methyl-iso-thiazolone etc.), stabilizers (e.g. DMSO), cofactors, emulsifiers (e.g. propanol), activators or measures to avoid undesired (side)reactions for the lipase determination are known to a person skilled in the art. In particular the additives and specifications described in DE 29 04 305 or EP 0 207 252 have proven to be suitable in this case. Lipase can be determined in samples of human as well as of animal origin (e.g. porcine pancreatic lipase) such as e.g. blood, serum or tissue.

The N-substituted carboxylic acid amide compounds or salts according to the invention according to the general formula (I) or (Ia) are produced by methods known to a person skilled in the art. In addition the compounds according to the invention such as for example tetrasodium N-(1, 2-dicarboxyethyl)-N-alkylsulfosuccinamide (REWOPOL B 2003) can be obtained commercially from known companies such as the Witco Surfactants GmbH Company, Steinau.

A further subject matter of the invention is a reagent or reagent kit for the determination of lipase which is essentially composed of the following components: (a) a lipase colour substrate, (b) a suitable buffer substance as well as (c)—contained in any desired partial reagent—a lower molecular N-substituted carboxylic acid amide derivative i.e. for example a compound according to the general formula (I) or (Ia). All known buffers are suitable as a buffer substance which are able to set a pH value between 6.0 and 10.5 in the reagent according to the invention. The preferred range of pH values lies between 7.0 and 9.5. Examples of suitable buffers are diethanolamine buffer, triethanolamine buffer, Tris or tartrate buffer or so-called Good's buffers such as Hepes buffer, bicine buffer, Taps buffer and CHES buffer (2-(cyclohexylamino)-ethanesulfonic acid buffer). Bicine buffer is particularly preferred. In this case the buffer concentration is usually between 5 and 200 mM preferably between 30 and 100 mM and quite especially preferably ca. 50 mM.

It has proven to be advantageous when the reagent is composed of two reagent components in which, in addition to other additives known to a person skilled in the art, the carboxylic acid amide derivative according to the invention is present in the first and the lipase colour substrate is contained in the second partial reagent. In this case it is essential that—before the determination—the carboxylic acid amide compound according to the invention is kept in a weakly alkaline buffered medium and the lipase colour substrate is kept at an acidic pH value. A particularly preferred embodiment of the reagent according to the invention is composed of two partial reagents in which the first has a weakly alkaline buffered pH value (pH 7.5 to 9.0, preferably ca. pH 8.0) as well as one or several carboxylic acid amide compounds according to the invention of the general formula (I) or (Ia) and further salts, preservatives and detergents. The second partial reagent contains a substance which is essentially buffered in a pH range of 2.0 to 5.0, preferably ca. pH 4.0, a suitable lipase substrate as well as optionally further auxiliary substances. For such a second partial reagent it has proven to be particularly advantageous to add emulsifiers such as for example cholate compounds and/or Thesits under pressure by means of an injection technique. For this the oil phase is preferred i.e. reagent R2 which contains all components is injected through a very fine cannula into an aqueous phase that is added first. As a result a clear, nonturbid emulsion/suspension with improved stability is obtained by the described method. Moreover the reagent is incapable of undesired side-reactions—due for example to the presence of unspecific enzymes (non-lipase esterases). Such a lipase substrate reagent characterized by a uniform particle size can be stored between 12 and 18 months at ca. 2 to 8° C. without loss of quality. This additionally ensures an appropriate stability of the complete reagent. The maximum size distribution of the particles is preferably ca. 100 nm which corresponds to a turbidity of less than 300 NTU (nephelometric turbidimetric unit).

number of value pairs: 25

BaPay=57.8108+1.0315*x(r=0.9828)

line of identity y=x x human sera

Figure 2:
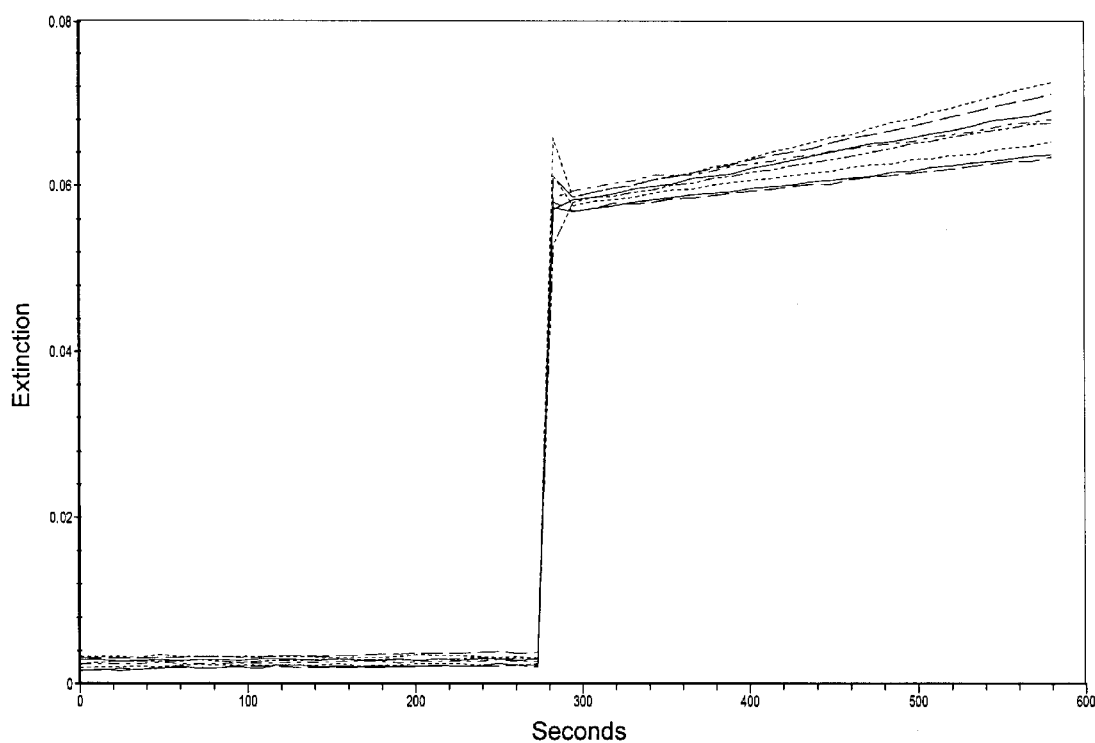
FIG. 2 is a graph of the IgG gradation 0–3 g/dl, R1 containing 0.27% (w/v) tetrasodium-N-(1,2-dicarboxyethyl)-Nalkyl-sulfosuccinamide, sample: 10 μl, other details as in the legend to FIG. 1.
Figure 3:
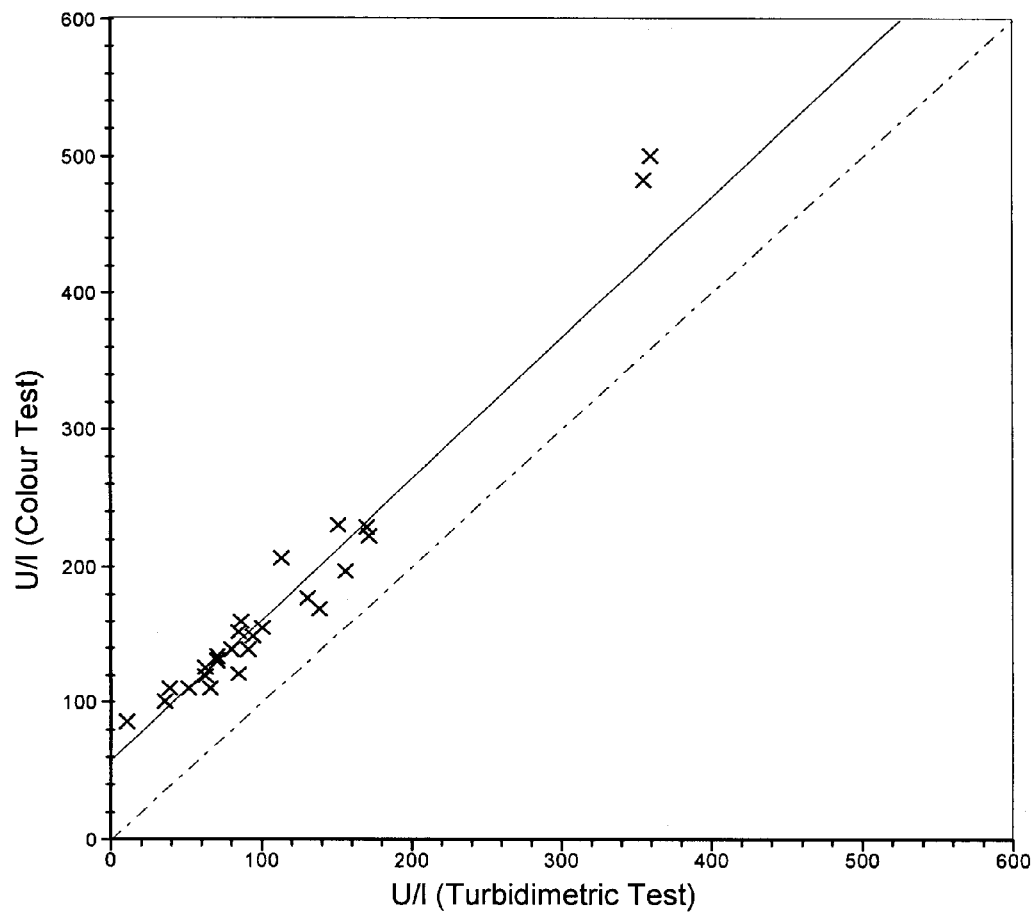
FIG. 3 is a graph of the results of the lipase, turbidimetric and colour test; R1/R2 without addition of the compound according to the invention; calibrator: Cfas (=calibrator for automated systems)
Figure 4:
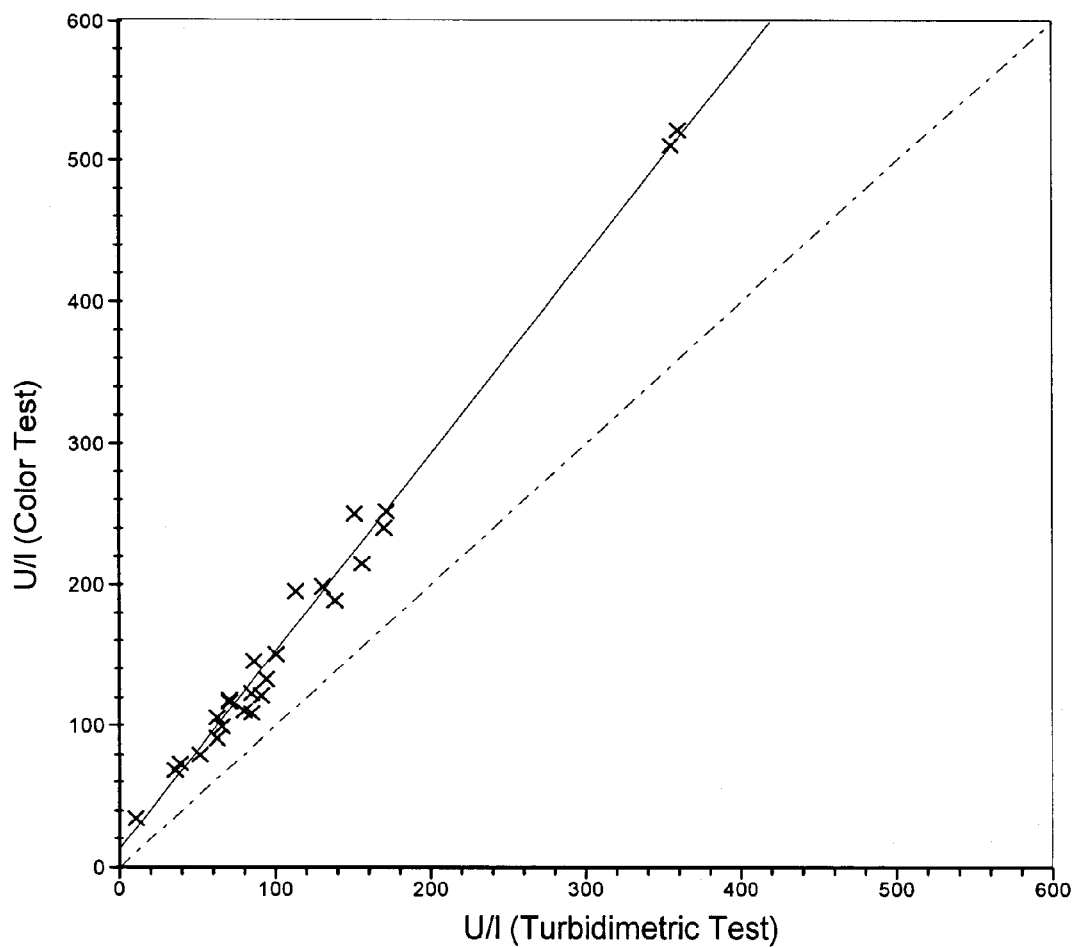

FIG. 4 is a graph showing the results of the lipase turbidimetric and colour test; R1 without, R2 with the compound according to the invention as in FIG. 2; other details as in the legend to FIG. 3 number of value pairs: 25

BaPa v=12.6916+1.3995*x(r=0.9944)

hour Hk y=9.4818+1.4178*x line of identity y=x x human sera

DETAILED DESCRIPTION OF THE INVENTION

The invention is elucidated further by the following examples:

EXAMPLE 1

Various concentrations of IgG as the sample

Reagent composition of the lipase colour test:

Reagent 1 (R1): 4.55 mmol/l taurodeoxycholate 1.77 mmol/I sodium deoxycholate 50.00 mmol/l bicine buffer 0.98 mg/l colipase 5.00 mmol/l calcium chloride preservative Reagent 2 (R2): 8.1 mmol/l taurodeoxycholate 0.24 mmol/l colour substrate (1,2-O-dilauryl-rac-glycero-3-glutaric acid-(6'-methyl resorufin) ester)

1.60 mmol/l tartrate buffer 0.10 mmol/l calcium chloride preservative/surfactant Samples: NaCl containing various concentrations of IgG (0–3 g/l)

Procedure for the colour test on a BM/Hitachi 717 automated analyzer according to the following application:

| PROGRAM 2 CHEMISTRY PARAMETERS | |
|---|---|
| TEST | Lipase |
| ASSAY CODE (RATE A) | 5–32–39 |
| SAMPLE VOLUME (μl) | 7–3 |
| R 1 volume (μl) | 250–100–0 |
| R 2 volume (μl) | 50–50–0 |
| WAVELENGTH (nm) | 800 570 |
| CALIB. Method | 2–0–0 |
| Std. 1 CONC. POS. | 0–1 |
| Std. 2 CONC. POS. | assigned value–2 |
| Std. 3 CONC. POS. | 0–0 |
| Std. 4 CONC. POS. | 0–0 |
| Std. 5 CONC. POS. | 0–0 |
| Std. 6 CONC. POS. | 0–0 |
| SD LIMIT | 0.1 |
| DUPLICATE LIMIT | 100 |
| SENSITIVITY LIMIT | 0 |
| ABS. LIMIT (INC/DEC) | 32000–0 |
| PROZONE LIMIT | 0–0 |
| EXPECTED VALUE (mg/dl) | 0–190 |
| PANIC VALUE (mg/dl) | — |
| INSTRUMENT FACTOR | 1.0 |

Evaluation: By reading off from a calibration curve which was also determined under the instrument conditions described above with the aid of a zero standard and a lipase standard (Cfas) from the Boehringer Mannheim Co.

Figure 1:
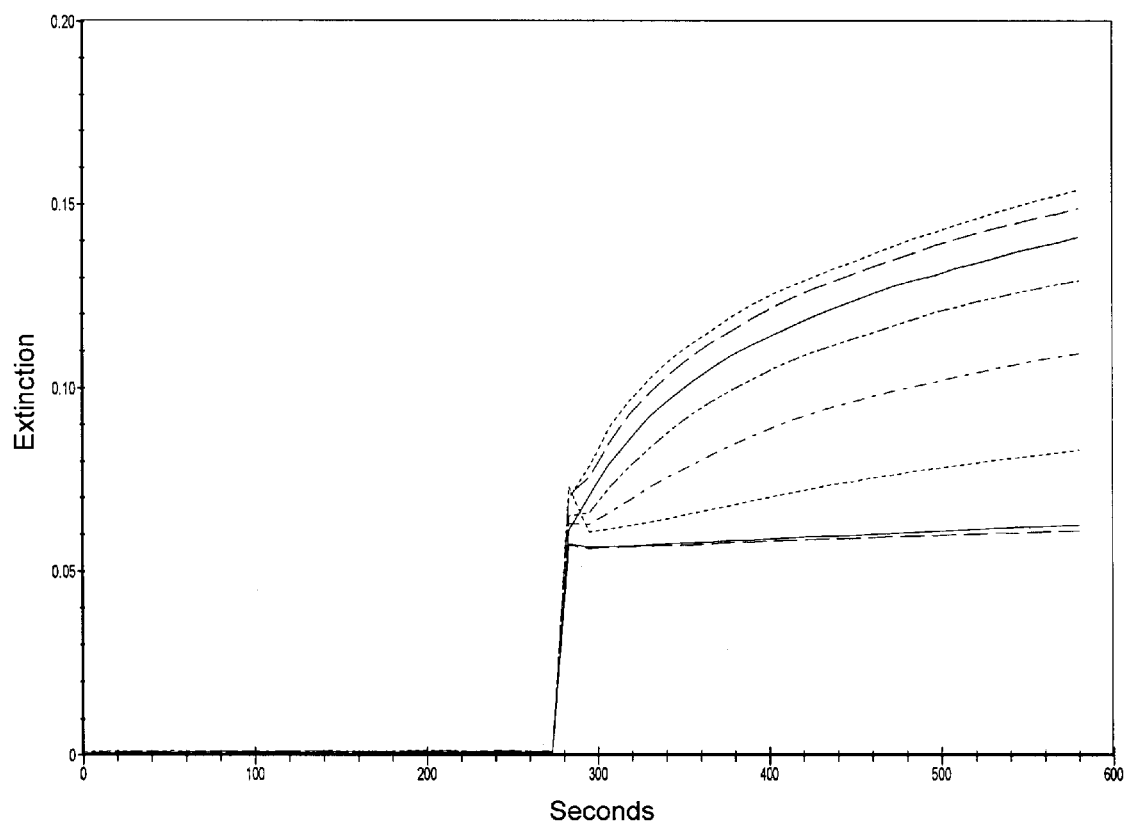
FIG. 1 is a graph showing IgG gradation 0–3 g/dl; R1 (reagent 1) without addition of the compound according to the invention, sample: 5 μl, blank NaCl—IgG 0,—IgG 0.5 g/dl, IgG 1.0 g/dl,—IgG 1.5 g/dl, IgG 2.0 g/dl,—IgG 2.5 g/dl, IgG 3.0 g/dl.

Result: It turned out that a hydrolysis of the colour substrate occurred which was clearly dependent on the concentration of the added IgG's in the case of an emulsion which did not contain a substance according to the invention (cf. FIG. 1).

EXAMPLE 2

Various concentrations of the additive according to the invention (interference eliminating agent)

The reagent composition for the lipase colour test corresponds to the reagents R1 and R2 stated in example 1 except that R1 additionally contains 0.27% of a mixture of tetrasodium-N-(1,2dicarboxyethyl)-N-alkyl-sulfosuccinamide with a C12 to C18 alkyl residue.

Samples: NaCl with various concentrations of IgG (0–3 g/l).

The colour test is carried out and evaluated on a BM/Hitachi 717 automated analyzer according to the application and details described in example 1.

Result: At the predetermined concentrations an unspecific non-enzymatic hydrolysis is eliminated (cf. FIG. 2).

EXAMPLE 3

Preparation of the complete reagent

Regant 1: as described in example 1

Reagent 2:

0.6 g lipase colour substrate (e.g. 1,2-O-dilauryl-rac-glycero-3-glutaric acid-(6'-methyl resorufin)ester) are solved in 9 ml of a suitable alcohol, e.g. ethanol. 1 g of a emulgator, e.g. Brij 35 or Triton X-114, is added to the solution. The resulting oelic phase is soaked up in an injection needle and pressed under high pressure through a thin cannula (inner diameter 0,15 to 1,0 mm) into an aqueous solution which is stirred at the same moment. The aqueous solution comprises, e.g., 0.15 g tartrate buffer (pH 5,0), 0.009 g calcium chloride and 0.5 g taurodeoxycholate solubilized in 100 ml water. It is possible that the aqueous solution contains in addition one or more preservative and any further auxiliary emulgator components.

EXAMPLE 4

Comparison of the turbidimetric method/colour test without the addition of a substance according to the invention.

The reagent composition of the lipase colour test corresponds to the details described in example 1.

The reagent composition of the "lipase turbidimetric test" is as follows:

R1: 19.0 mmol/l sodium deoxycholate 26.0 mmol/l Tris buffer 3.0 mg/ml colipase 0.1 mmol/l calcium chloride 0.30 mmol/l triolein preservative Samples: human sera The various lipase determinations are carried out on a BM/Hitachi 717 automated analyzer according to the following application:

Colour test
temperature: 37° C.
PROGRAM 2 CHEMISTRY PARAMETERS

| TEST | Lipase |
|---|---|
| ASSAY CODE (RATE A) | 5–32–39 |
| SAMPLE VOLUME (μl) | 7–3 |
| R 1 volume (μl) | 250–100–0 |
| R 2 volume (μl) | 50–50–0 |
| WAVELENGTHS (nm) | 800 570 |
| CALIB Method | 2–0–0 |
| STD: 1 CONC. POS. | 0–1 |
| STD: 2 CONC. POS. | assigned value–2 |
| STD: 3 CONC. POS. | 0–0 |
| STD: 4 CONC. POS. | 0–0 |
| STD: 5 CONC. POS. | 0–0 |
| STD: 6 CONC. POS. | 0–0 |
| SD LIMIT | 0.1 |
| DUPLICATE LIMIT | 100 |
| SENSITIVITY LIMIT | 0 |
| ABS: LTMIT (INC/DEC) | 32000–0 |
| PROZONE LIMIT | 0–0 |
| EXPECTED VALUE (mg/dl) | 0–190 |
| PANIC VALUE (mg/dl) | — |
| INSTRUMENT FACTOR | 1.0 |

Turbidimetric test
temperature: 37° C.
PROGRAM 2 CHEMISTRY PARAMETERS

| TEST | Lipase |
|---|---|
| MEAS. METHOD (KTNETIC A) | 5–30–50 |
| SAMPLE VOLUME pl) | 10–2 |
| R 1 volume (μl) | 250–20–0 |
| R 2 volume (μl) | 0–20–0 |
| WAVELENGTH (nm) | 660–340 |
| CALIBRATION | 1–0–0 |
| STD: 1 CONC. POS. (U/l) | 0–1 |
| | (μcat/l) 0.00–1 |
| STD: 2 CONC. POS. | assigned value–2 |
| STD: 3 CONC. POS. | 0–0 |
| STD: 4 CONC. POS. | 0–0 |
| STD: 5 CONC. POS. | 0–0 |
| STD: 6 CONC. POS. | 0–0 |
| SD LIMIT | 0.1 |
| DUPLICATE LIMIT | 100 |
| SENSITIVITY LIMIT | 0 |
| ABS LIMIT (INC/DEC) | 10000–0 |
| PROZONE LIMIT | 0–0 |
| NORMAL RANGE (U/l) | 0–190 |
| PANIC VALUE (U/l or μg/cat/l) | (μg/cat/l) 0.00–3.17 — |
| INSTRUMENT FACTOR | 1.0 |

The evaluation is carried out analogously to example 1.

Result: The method comparison shows that colour tests exhibit an axis intercept which is due to the unspecific hydrolysis of the colour substrate by serum components (cf. FIG. 3).

EXAMPLE 5

Comparison of the turbidimetric method/colour test with the addition of the substance according to the invention.

The reagent composition and procedure are as described in example 4. In addition tetrasodium-N-(1,2-dicarboxyethyl)-N-octadecanyl-sulfosuccinimate or an appropriate mixture containing the substance at a concentration of 0.27% (w/v) reagent 1 (R1) was added as the substance according to the invention.

Samples: human sera

The various lipase determinations were carried out on a BM/Hitachi 717 automated analyzer according to the application stated in example 4. The evaluation was also carried out analogously to examples 4 and 1.

Result: The addition of the substance according to the invention eliminates unspecific reactions and thus eliminates the axis intercept compared to the turbidimetric method (FIG. 4).

We claim:

1. A method for determining lipase in a biological sample comprising adding a lipase color substrate and subsequently photometrically determining the dye released from the substrate, wherein the determination is carried out in the presence of a lower molecular N-substituted carboxylic acid amide derivative.

2. The method of claim 1, wherein said lower molecular N-substituted carboxylic acid amide derivative is a compound of formula (I)

(I)

wherein $R^1$ and $R^2$ are independently hydrogen or a saturated or unsaturated, substituted or unsubstituted hydrocarbon residue with 2 to 24 carbon atoms;

Z is a saturated or unsaturated, substituted or unsubstituted, cyclic or straight-chained hydrocarbon residue with 1 to 10 carbon atoms;

X is an atom or a group of atoms with positive charge; and n is a number from 1 to 3.

3. The method of claim 2, wherein $R^1$ or $R^2$ are independently an optionally substituted alkyl, aryl, alkylaryl or alkylene group comprising 3 to 24 C atoms; and wherein Z is a methylene or ethylene group with up to 10 C atoms.

4. The method of claim 2, wherein Z is substituted with a carboxyl or sulfonyl group.

5. The method of claim 2, wherein at least one of $R^1$ and $R^2$ is selected from the group consisting of methyl, ethyl, propyl, butyl, pentyl, ethylenyl, propylenyl, and a C12 to C18 alkyl group.

6. The method of claim 1, wherein the lower molecular N-substituted carboxylic acid amide derivative is selected from the group consisting of a tetrasodium-N-(1,2dicarboxylethyl)-N-alkyl-sulfosuccinamide, a tetrasodium-N-(1,2-dicarboxylethyl)-N-alkylarylsulfosuccinamide, derivatives thereof and mixtures thereof.

7. The method of claim 1, wherein said carboxylic acid amide derivative is present in the sample solution at a concentration of 0.0001 to 2.0% w/v.

8. The method of claim 1, wherein the compound or corresponding compounds are present at a final concentration of 0.01 to 1.0% w/v.

9. The method of claim 1, comprising determining a lipase selected form the group consisting of human pancreatic lipase and animal pancreatic lipase.

10. A reagent for the determination of lipase comprising a lipase substrate; a buffer substance; and a lower molecular N-substituted carboxylic acid amide derivative.

11. The reagent of claim 10 wherein the lower molecular N-substituted carboxylic acid amide derivative is a compound of formula (I):

(I)

wherein $R^1$ and $R^2$ are independently selected from the group consisting of hydrogen and a saturated or unsaturated, substituted or unsubstituted hydrocarbon residue with 2 to 24 carbons atoms;

Z is a saturated or unsaturated, substituted or unsubstituted, cyclic or straight-chained hydrocarbon residue with 1 to 10 carbon atoms, X is an atom or a group of atoms with a positive charge and n is a number from 1 to 3.

12. The reagent of claim 10, wherein the reagent comprises a first partial reagent and a second partial reagent, wherein said first partial reagent comprises a buffer substance with a pH value of ca. 7.5 to 9.0, the compound of formula (I), and a member selected from a detergent, a preservative and mixtures thereof; and wherein said second partial reagent comprises a buffer substance having a pH value of ca. 2.0 to 5.0, said lipase substrate and an emulsifier.

13. The reagent of claim 10, wherein said lower molecular N-substituted carboxylic acid derivative is selected from the group consisting of tetrasodium-N-(1,2-dicarboxyethyl-N-alkylsulfosuccinamide, tetrasodium-N-(1,2,-dicarboxyethyl)-N-alkylarylsulfosuccinamide, a corresponding derivative thereof and mixtures thereof.

14. A method for eliminating unspecific reactions in the determination of lipase in biological sample material comprising adding an N-substituted carboxylic acid amide derivative or a compound of formula (I):

(I)

wherein $R^1$ and R2 are independently hydrogen or a saturated or unsaturated, substituted or unsubstituted hydrocarbon residue with 2 to 24 carbon atoms;

Z is a saturated or unsaturated, substituted or unsubstituted, cyclic or straight-chained hydrocarbon residue with 1 to 10 carbon atoms;

X is an atom or a group of atoms with positive charge; and n is a number from 1 to 3 to the biological sample material to be tested.

15. The method of claim 2, wherein said carboxylic acid amide derivative is present in the sample solution at a concentration of 0.0001 to 2.0% w/v.

16. The method of claim 2, wherein the compound or corresponding compounds are present at a final concentration of 0.01 to 1.0% w/v.

17. The method of claim 3, wherein said carboxylic acid amide derivative is present in the sample solution at a concentration of 0.0001 to 2.0% w/v.

18. The method of claim 3, wherein the compound or corresponding compounds are present at a final concentration of 0.01 to 1.0% w/v.

19. The method of claim 6, wherein said carboxylic acid amide derivative is present in the sample solution at a concentration of 0.0001 to 2.0% w/v.

20. The method of claim 6, wherein the compound or corresponding compounds are present at a final concentration of 0.01 to 1.0% w/v.

* * * * *